United States Patent
Boehr et al.

(10) Patent No.: US 7,129,095 B2
(45) Date of Patent: Oct. 31, 2006

(54) METHOD AND SYSTEM FOR USING A WEIGHTED RESPONSE

(75) Inventors: Christopher Boehr, San Gabriel, CA (US); Shou-Hua Zhang, Arcadia, CA (US); Chang-Meng Hsiung, Irvine, CA (US)

(73) Assignee: Smiths Detection Inc., Pasadena, CA (US)

( * ) Notice: Subject to any disclaimer, the term of this patent is extended or adjusted under 35 U.S.C. 154(b) by 910 days.

(21) Appl. No.: 10/112,151

(22) Filed: Mar. 29, 2002

(65) Prior Publication Data

US 2003/0186461 A1    Oct. 2, 2003

(51) Int. Cl.
    *G01N 27/416*    (2006.01)
(52) U.S. Cl. .................. 436/151; 436/149; 436/150; 422/82.01; 422/82.05; 422/83; 422/98; 702/22; 702/23; 702/24; 702/25; 702/30; 702/32
(58) Field of Classification Search .......... 422/68.1, 422/82.01, 82.05, 83, 98; 436/8, 10, 149, 436/150–151; 702/19, 22–32, 57, 64, 65
See application file for complete search history.

(56) References Cited

U.S. PATENT DOCUMENTS

| 5,078,501 | A | * | 1/1992 | Hekker et al. ............ 359/561 |
| 5,469,369 | A | * | 11/1995 | Rose-Pehrsson et al. ..... 702/27 |
| 5,703,959 | A | * | 12/1997 | Asano et al. ............... 382/133 |
| 5,774,379 | A | * | 6/1998 | Gross et al. .................. 702/72 |
| 5,926,804 | A | * | 7/1999 | Tufts et al. ................... 706/25 |
| 5,976,466 | A | * | 11/1999 | Ratner et al. ............ 422/82.11 |
| 6,157,894 | A | * | 12/2000 | Hess et al. ................... 702/54 |
| 6,505,181 | B1 | * | 1/2003 | Lambert et al. ............. 706/20 |
| 6,834,237 | B1 | * | 12/2004 | Noergaard et al. ........... 702/19 |
| 6,895,338 | B1 | * | 5/2005 | Hsiung et al. ............... 702/22 |

FOREIGN PATENT DOCUMENTS

| WO | WO 97/14958 | 4/1997 |
| WO | WO 99/61902 | 12/1999 |

\* cited by examiner

*Primary Examiner*—Jill Warden
*Assistant Examiner*—Dwayne K. Handy
(74) *Attorney, Agent, or Firm*—Foley and Lardner LLP (57) ABSTRACT

The present invention is related to the sensing of analytes and in particular, to methods of determining, resolving, identifying, or quantitating such analytes once detected. This invention provides systems and methods for identifying analytes, comprising using an importance index to give greater weight to the responses from sensors that measure characteristics most useful for identification of analytes. In other aspects, the systems and methods are useful for increasing the stability of electronic nose systems by prolonging the predictive capability of the training set of known analytes. In still other aspects, the systems and methods are useful for detecting and responding to events correlated with the presence of an analyte.

7 Claims, 6 Drawing Sheets

METHOD AND SYSTEM FOR USING A WEIGHTED RESPONSE

BACKGROUND OF THE INVENTION

The present invention is related to the sensing of analytes in a medium or a vacuum, such as odors, smells, vapors and the like in air, and in particular, to systems and methods of determining, resolving, or identifying such analytes once detected.

One approach for sensing analytes is the use of an array of sensors on a substrate. Each sensor has a characteristic response to exposure to an analyte, such as an odor. The sensors can be connected to an electrical circuit for measuring the responses to the analyte. See, for example, U.S. patent application Ser. No. 09/130,775, filed Aug. 7, 1998 and assigned to the present assignee, which is incorporated by reference herein. Each sensor responds to a broad class of stimuli, with the collective response of the many different members of the sensor array providing a fingerprint of an analyte of interest.

Typically, each array contains sensors with varying compositions, each of which responds to certain properties of the analytes. The array is exposed to a panel of known analytes and pattern recognition algorithms are used to analyze the responses and to produce a fingerprint of the responses of known analytes (this data is called a training set). Next, the array is exposed to an unknown analyte and this response pattern is matched with that of the patterns from the training set to identify the unknown analyte. However, equal weighting of responses from all sensors in a particular array can be problematic. In practice, not all measurable properties of an analyte are useful for analyte identification. While certain characteristics vary widely between different analytes, other characteristics are very similar between analytes.

Thus there is a need for systems and methods that give greater weight to sensors that measure properties which are clearly distinguishable between two analytes. There is also a need for systems and methods that give greater weight to sensors which can reproducibly measure a particular property. Such systems and methods will enhance the ability of a sensor array to correctly identify analytes, as well as prolong the predictive capability of a training set by reducing the deleterious effects of sensor drift. This invention fulfills this and other needs.

BRIEF SUMMARY OF THE INVENTION

This invention provides systems and methods for identifying and quantitating analytes, comprising giving greater weight to the responses from sensors that measure characteristics most useful for identification of analytes. Such characteristics are those that are highly distinguishable between different analytes and that are capable of being reproducibly measured. The invention also provides methods for detecting and responding to events that are correlated with the presence of an analyte, as well as increasing the stability of sensor array systems by prolonging the predictive capability of a training set.

In certain aspects, the present invention relates to methods for identifying an analyte comprising: a) disposing a plurality of d sensors in an array, each sensor having a different response to the analyte; b) exposing the d sensors to the analyte to generate a response vector for the analyte; c) applying an importance index vector to the response vector to generate a weighted response vector; and d) comparing the weighted response vector to a weighted training set and thereafter selecting the best match to identify the analyte.

Preferably, the importance index vector is generated after a training mode conducted on the d sensors and before identification of the analyte. In other embodiments, the importance index vector is generated after a training mode conducted on a device different from the d sensors.

The training mode comprises: a) exposing d sensors two or more times to each of a plurality of known analytes and measuring the responses from each sensor to each exposure to create a training set, wherein the training set contains a response vector for each exposure to each of the plurality of known analytes; b) normalizing and scaling the response vectors for each exposure to the plurality of known analytes; and c) performing cross-validation on the training set.

The importance index vector is the collection of importance indices for each sensor and the weighted training set is generated by application of the importance index vector to the response vector for each exposure to the plurality of known analytes in a training set.

In preferred embodiments, the importance index for a particular sensor is calculated from all the responses by that sensor in a training set as follows:

$$\sqrt{\frac{s^2_{OverallAmongAnalytes}}{s^2_{OverallWithinAnalytes}}} \qquad \text{I}$$

wherein $s^2_{OverallAmongAnalytes}$ is the overall variance for responses by that sensor among the analytes and $s^2_{OverallWithinAnalytes}$ is the overall variance for responses by that sensor within the analytes.

$s^2_{OverallAmongAnalytes}$ equals:

$$\frac{1}{k-1} \sum_{i=1}^{k} (\bar{x}_i - \bar{\bar{x}})^2 \qquad \text{Ia}$$

and $s^2_{OverallWithinAnalytes}$ equals:

$$\frac{1}{k} \sum_{i=1}^{k} \sum_{j=1}^{m(i)} \frac{(x_{ij} - \bar{x}_i)^2}{m(i) - 1} \qquad \text{Ib}$$

k is the number of analytes in the training set;

i is an index over analytes in the training set and ranges from 1 to k;

m(i) is the number of exposures in the training set for the i th analyte;

j represents an exposure number in the training set to the i th analyte, and ranges from 1 to m(i);

$x_{ij}$ is the response in the j th exposure to the i th analyte in the training set for the sensor whose importance index is being calculated;

$\bar{x}_i$ is the mean value of all exposures in the training set to the i th analyte for the sensor whose importance index is being calculated; and $\bar{x}$ is the mean value of all responses in the training set for the sensor whose importance index is being calculated.

In preferred embodiments, the application of an importance index vector to a response vector to generate a weighted response vector comprises: a) raising the importance index for each sensor to a certain power; b) multiplying each response in the response vector by the importance index for the corresponding sensor raised to a certain power to yield a weighted response; and c) assembling the weighted responses to generate a weighted response vector. Typically, the application of the importance index to the training set to generate a weighted training set is comprised of the following steps for each response vector in the training set: a) raising the importance index for each sensor to a certain power; b) multiplying each response by the importance index for the corresponding sensor raised to a certain power to yield a weighted response; and c) assembling the weighted responses to generate a weighted response vector. Preferably, the importance index is raised to the first power.

In other embodiments, the methods further comprise data processing steps including, but not limited to, noise filtering, noise reduction, normalization, mean-centering, variance scaling, autoscaling, or combinations thereof. These data processing steps normally occur prior to calculation of the importance index.

In preferred embodiments, the weighted response vector obtained from an unknown vapor is compared to the weighted response vectors in the training set using a pattern recognition algorithm. Such algorithms include, but are not limited to, Principal Component Analysis, Fisher Linear Discriminant Analysis, Partial Least Squares Discriminant Analysis, Support Vector Machine Analysis, Kernel Fisher Discriminant Analysis, Soft Independent Modeling of Class Analogy (SIMCA), K-nearest Neighbors, Canonical Discriminant Analysis, neural networks, genetic algorithms, and fuzzy logic.

In especially preferred embodiments, the analyte is an odor, each of the sensors has an electrical response to the analyte, and the d sensors are disposed on a single substrate.

The sensor array can comprise at least one sensor, including, but not limited to, thermal sensors, radiation sensors, mechanical sensors, magnetic sensors, chemical sensors, inorganic metal oxide semiconductor sensors, mass-sensitive piezoelectric sensors, nonconducting/conducting regions sensors, surface acoustic wave devices, tin oxide detectors, conducting organic polymers, dye-impregnated polymer films on fiber optic detectors, polymer-coated micromirrors, quartz crystal microbalances, electrochemical gas detectors, chemically sensitive field-effect transistors, carbon black-polymer composite chemiresistors, and combination thereof.

In another aspect, the invention provides systems for identifying an unknown analyte comprising: a) a sensor array having a plurality of d sensors wherein each sensor has a different response to the analyte; b) a sensor array interface for detecting the response of each sensor upon exposure of the d sensors to the analyte; and c) a computer for generating a response vector for the analyte, applying an importance index vector to the response vector to generate a weighted response vector, and comparing the weighted response vector to the weighted training set, and thereafter selecting the best match to identify the unknown analyte.

In another aspect, the invention provides methods for identifying an unknown analyte using a combination of sensor selection and sensor weighting. The methods comprise: a) disposing a plurality of d sensors in an array, each having a different response to different analytes; b) exposing the d sensors two or more times to a plurality of known analytes and measuring the responses from each sensor to each exposure to create a first training set, wherein the first training set contains a response vector for each exposure to the plurality of known analytes; c) generating a first importance index for each sensor; d) selecting a subset of sensors having first importance indices above a certain threshold; e) generating a second training set consisting of all the response vectors in the first training set but with responses to those sensors not passing the selection criterion removed; f) calculating a second importance index based on the second training set and assembling a revised second importance index vector; g) applying the second importance index vector to the second training set to generate a weighted second training set; h) exposing the subset of sensors to the unknown analyte to generate a response vector for the unknown analyte; i) applying the second importance index vector to the response vector for the unknown analyte to obtain a weighted response vector; and j) comparing the weighted response vector to the second weighted training set, and then selecting the best match thereby identifying the unknown analyte.

In yet another aspect, the invention comprises methods for identification of analytes using sensor selection. The methods comprise: a) disposing a plurality of d sensors in a array, each having a different response to different analytes; b) exposing the d sensors two or more times to a plurality of known analytes and measuring the responses from each sensor to each exposure to create a first training set, wherein the first training set contains a response vector for each exposure to each of the plurality of known analytes; c) generating an first importance index for each sensor; d) identifying a subset of sensors with importance indices above a certain threshold; e) generating a second training set consisting of all the response vectors in the first training set but with responses to those sensors not passing the selection criterion removed; f) exposing the subset of selected sensors to the unknown analyte to generate a response vector; and g) comparing the response vector for the unknown analyte to response vectors in the second training set, and thereafter selecting the best match to identify the unknown analyte.

In another aspect, the invention provides methods for quantifying the concentration of an analyte. The methods comprise: a) disposing a plurality of d sensors in an array, each sensor having a different response to changes in concentration of an analyte; b) exposing the d sensors to the analyte to generate a response vector for the analyte; c) applying an importance index vector to the response vector to generate a weighted response vector; and d) comparing the weighted response vector to a weighted training set, wherein the training set comprises the responses to the analyte at different concentrations and then selecting a match to quantify the concentration of the analyte.

In yet another aspect, the invention provides methods for detecting and responding to an event. The methods comprise: a) disposing a plurality of d sensors in an array, each sensor having a different response to an analyte, wherein the presence of the analyte is correlated with the occurrence of an event; b) exposing the d sensors to the analyte to generate a response vector for the analyte; c) applying an importance index vector to the response vector to generate a weighted response vector comparing the weighted response vector to a weighted training set; d) selecting a match to identify the analyte; and d) responding to the event correlated with the presence of the analyte.

In still yet another aspect, the invention provides methods for prolonging the predictive capability of a training set for a sensor array. The methods comprise: a) disposing a plurality of d sensors in an array, each sensor having a different response to different analytes; b) exposing the d sensors two or more times to a plurality of known analytes and measuring the responses from each sensor to each exposure to create a training set, wherein the training set contains a response vector for each exposure to the plurality of known analytes; c) calculating an importance index for each sensor and generating an importance index vector; and d) applying the importance index vector to the training set to create a weighted training set, thereby prolonging the predictive capability of the training set.

In another aspect, the invention provides methods for increasing the stability of systems with sensor arrays. The methods comprise: a) disposing a plurality of d sensors in an array, each sensor having a different response to different analytes; b) exposing the d sensors two or more times to a plurality of known analytes and measuring the responses from each sensor to each exposure to create a training set, wherein the training set contains a response vector to each of the plurality of known analytes; c) calculating an importance index for each sensor and generating an importance index vector; and d) applying the importance index vector to the training set to create a weighted training set.

These and other aspects of the present invention will become more readily apparent when read with the accompanying figures and detailed description.

DEFINITIONS

The term "response vector" refers to the collection of the responses from all of the sensors during exposure to a particular analyte.

The term "weighted response vector" refers to a response vector to which an importance index has been applied.

The term "importance index", "iip", or "weighting factor" refers to a number associated with a particular sensor that is a measure of the ability of the sensor to discriminate and correctly identify one of a particular set of analytes to which the sensor has been exposed repeatedly. Importance indices are generally positive real numbers and can be used either to assign greater weight to the responses from sensors that provide the best discrimination and predictive ability, or to select the optimal sensors for detection of analytes. In the trade, the term "discrimination power" is also used to refer to what is defined herein as "importance index".

The term "importance index vector" as used herein refers to the collection of the importance indices for all sensors in an array.

The term "discrimination" refers to the ability to measure a parameter that distinguishes a certain analyte from other analytes.

The term "predictive ability" or "predictive capability" refers to the ability to correctly identify a certain analyte based upon the data from all sensors of the array.

The term "training set" refers to the set of data (i.e., response vectors) generated during the repeated exposure of the sensor set to a collection of known analytes.

The term "weighted response vectors in a training set" or "weighted training set" refers to a training set to which an importance index has been applied.

The term "training mode" refers to a period of time prior to exposure of a sensor array to an unknown analyte during which the response data for a set of known analytes is collected. The response data collected during this training mode is called a training set and can be used at a later time to identify unknown analytes.

The term "normalizing" or "normalization" refers to the processing of data to remove the variation in the magnitude of sensor responses due to the effects of differences in concentration. Normalization can be conducted using a simple weighting method, such as $$normalized(R/R_o)_i = (R/R_o)_i \bigg/ \sum_i (R/R_o)_i. \qquad \text{II}$$

where i specifies sensor number from 1 to the number of sensors.

The term "scaling" refers to any method used to remove inadvertent weighting of the responses from a sensor that arise due either to differences in the average magnitude of the response for a particular sensor or to arbitrary units. Common scaling methods include mean centering, variance scaling, and autoscaling (mean centering followed by variance scaling).

The term "cross-validation" refers to a process for determining the quality of a training set. In one aspect, the process is as follows: 1) expose all sensors multiple times to each of a set of known analytes and generate a training set, 2) remove a subset of the response vectors from the training set (preferably at least one exposure to each analyte) leaving the remaining response vectors to form a new training set, 3) use a pattern recognition algorithm to identify the response vectors pulled out of the original training set in step 2 by comparison to the new training set, and 4) repeat steps 2 and 3 until all response vectors in the training set have been removed and identified. If most training set exposures can be correctly identified using this procedure, then the training set is considered to be "well-behaved" and thus suitable for correct identification of unknown analytes.

BRIEF DESCRIPTION OF THE DRAWINGS

In the following descriptions of the figures, the term "iip" is defined as the power to which all importance indices are raised before being multiplied by responses in a response vector.

FIG. 5A shows results using Canonical Discriminant Analysis as the pattern recognition algorithm; FIG. 5B shows results using the KNN algorithm. The X-axis shows the value of iip.

DETAILED DESCRIPTION

I. Introduction

This invention provides systems and methods for identifying analytes, comprising use of an importance index, which is a measure of the distinctiveness of the particular characteristic measured by a sensor and the reproducibility by which the characteristic can be measured.

Arrays of sensors with different polymer compositions are particularly valuable for identifying analytes. Due to variations in polymer composition, each sensor is responsive to a particular characteristic of an analyte. For example, a sensor with a hydrophobic polymer is particularly responsive to a hydrophobic analyte, but not to a hydrophilic analyte. However, not all characteristics measured by the different sensors are useful for analyte identification. While certain characteristics, such as hydrophobicity and vapor pressure, vary widely between analytes, other characteristics, such as molecular weights, are very similar between analytes. Use of these similar characteristics in analysis can lead to misidentification of analytes. Advantageously, this invention circumvents this problem by focusing on those sensors which measure highly distinguishable characteristics. For example, a sensor attuned to the hydrophobicity of an analyte would be more important for an analyte set with some hydrophobic analytes and some hydrophilic analytes, than for an analyte set with all hydrophobic or all hydrophilic analytes.

In one embodiment, the systems and methods of this invention comprise application of an importance index to give greater weight to sensors which measure highly distinctive characteristics. Typically, the array is exposed to a panel of known analytes two or more times, responses are collected, and the data is reduced to create a training set. Next, an importance index is calculated for each sensor and applied to the response vectors in the training set. Cross validation is then performed to estimate the quality of the training set by employing a pattern recognition algorithm to attempt to identify small subsets of the training set against the remainder of the training set. Finally, in the identification mode, the array is exposed to an unknown analyte, the responses are collected, the data is processed, the importance index is applied, and the resulting weighted response pattern for the unknown analyte is matched with the weighted responses in the training set to identify the unknown analyte or the class of analyte.

In another embodiment, the importance index or weighting factor is used to identify sensors which measure the most highly distinguishable characteristics. The analytes are then tested using only these sensors, rather than using all sensors, some of which will measure less distinguishable characteristics.

In another aspect, the systems and methods comprise both the use of an importance index to select the optimal sensors and weighting of the sensors with a revised importance index based on the data from the optimal subset of sensors. Typically, these systems and methods comprise selection of a desired threshold for the importance index, exclusion of the responses from a particular sensor if that sensor's importance index is less than the threshold, assembly of a revised training set containing data only from the subset of sensors whose importance index is greater than or equal to the threshold (preferably, solely containing data from this subset), re-processing of the revised training set (including both renormalization and rescaling), re-calculation of the importance index vector, re-application of the importance index vector to the revised training set to form a revised weighted training set, exposure to an unknown analyte, collection of data, application of the revised importance index vector to the response to the unknown analyte, and application of a pattern recognition algorithm to identify the unknown analyte.

In another aspect, the invention provides systems and methods for quantifying the concentration of an analyte. Typically, the systems and methods use sensors which have different responses to changes in concentration of an analyte. These sensors are exposed to an analyte to generate a response vector. Next, an importance index vector is applied to the response vector to generate a weighted response vector. In order to determine the concentration of the analyte, this weighted response vector is compared to a weighted training set that comprises the responses to the analyte at different concentrations. In certain embodiments, each sensor provides a first electrical response when the sensor is contacted with a first fluid comprising a chemical analyte at a first concentration, and a second electrical response when the sensor is contacted with a second fluid comprising the same chemical analyte at a second different concentration. The response can be, for example, resistance, impedance, capacitance, or voltage. The first and second fluids may reflect a change in the concentration of an analyte in a fluid sampled at two time points. The sensor array preferably comprises sensors which respond differently to a change in an analyte concentration, i.e., the difference between the first and second electrical response of one sensor is different from the difference between the first and second electrical response of another sensor.

In yet another aspect, the invention provides systems and methods for detecting and responding to an event. Typically, the systems and methods comprise exposing sensors to an analyte whose presence is correlated with the occurrence of an event. A response vector is generated and then an importance index vector is applied to the response vector to generate a weighted response vector. This weighted response vector is compared to a weighted training set in order to identify the analyte. The appropriate response to the event correlated with presence of the analyte is then initiated.

In other aspects, the systems and methods are useful for prolonging the predictive capability of the training set of known analytes. By giving greater weight to sensors that measure highly distinctive traits with high reproducibility, the systems and methods of the present invention reduce the effect of sensor drift on the predictive ability of a sensor array. By prolonging the predictive capability of the training set, the invention increases the stability of sensor array systems.

It will be apparent to one of skill in the art that combinations of the above systems and methods can be employed.

II. Training Mode

In certain aspects, the importance index is calculated directly after a training period during which the characteristics of a variety of known analytes are measured. This information is stored and used as a guideline for identifying unknown analytes in the "identification mode".

In certain embodiments, the training mode comprises exposing an array of sensors two or more times to each known analyte, measuring the responses from each sensor for each exposure, and assembling the responses for one exposure into a response vector. The collection of response vectors taken in training mode is called a training set. In order to ensure that the training set is suitable for identification of unknown analytes, the data is typically processed and cross-validated. In preferred embodiments, the data is normalized and scaled prior to cross-validation.

III. Calculation of the Importance Index

Once a training set is assembled, an importance index for each sensor with respect to a certain set of known analytes is calculated using the data from the training set assembled from multiple exposures to that set of analytes. The importance indices for all sensors are assembled into an importance index vector. This importance index vector can either be used as a factor to weigh the training set, as a guide for choosing the optimal sensors for detection of certain analytes, or for combinations thereof.

A. Definition of the Importance Index

In certain preferred systems and methods of this invention, the importance index for a particular sensor is calculated from all the responses by that sensor in a training set as follows:

$$\sqrt{\frac{s^2_{OverallAmongAnalytes}}{s^2_{OverallWithinAnalytes}}} \quad \text{I}$$

$s^2_{OverallAmongAnalytes}$ is the overall variance among analytes for responses by a sensor in the training set, which is a measure of the degree of difference between analytes.

Specifically, $s^2_{OverallAmongAnalytes}$ equals:

$$\frac{1}{k-1}\sum_{i=1}^{k}(\bar{x}_i - \bar{\bar{x}})^2. \quad \text{Ia}$$

$s^2_{OverallWithinAnalytes}$ is the overall variance within analytes for responses by a sensor, which is a measure of the consistency of the responses from that sensor to the known analytes.

Specifically, $s^2_{OverallWithinAnalytes}$ equals:

$$\frac{1}{k}\sum_{i=1}^{k}\sum_{j=1}^{m(i)}\frac{(x_{ij}-\bar{x}_i)^2}{m(i)-1}. \quad \text{Ib}$$

In the above equations, k is the number of analytes in the training set; i is an index that indicates a particular analyte in the training set and ranges from 1 to k; m(i) is the number of exposures in the training set for the i th analyte; j represents an exposure number in the training set to the i th analyte, and ranges from 1 to m(i); $x_{ij}$ is the response in the j th exposure to the i th analyte in the training set for the sensor whose importance index is being calculated;

$$\bar{x}_i$$

is the mean value of all exposures in the training set to the i th analyte for the sensor whose importance index is being calculated; and $$\bar{\bar{x}}$$

is the mean value of all responses in the training set for the sensor whose importance index is being calculated.

The importance index is generally a positive real number and is specific to a certain sensor with respect to a certain set of known analytes. A sensor with a large $s^2_{OverallAmongAnalytes}$ generates responses with large distinctions between analytes, and a sensor with a small $s^2_{OverallWithinAnalytes}$ generates a more consistent response to each analyte. The importance index, which is defined as the ratio of $s^2_{OverallAmongAnalytes}$ to $S^2_{OverallWithinAnalytes}$, is a combination of the two factors into a single numerical value. Preferably, the higher the importance index, the more valuable the data from the corresponding sensor for identification of analytes.

B. Application of the Importance Index

In certain systems and methods of the present invention, the importance index for each sensor is used as a weighting factor for the responses from that particular sensor to a particular set of analytes. Preferably, the importance index is raised to a power greater than zero and multiplied with a normalized and/or scaled sensor response. Each element of the weighted response vector (one element for each sensor) is equal to the value for the same sensor in the unweighted response vector multiplied by the importance index for that sensor raised to any power greater than zero. In operation, the greatest distinction between analytes arises when the response is multiplied by the importance index raised to the first power. Preferably, the importance index is raised to the first power.

The importance index is applied both to response vectors in a training set and to response vectors from unknown analytes exposed during identification mode. In certain preferred embodiments, each importance index is raised to the same power, and that power is used both when applied to the training set after completion of training mode, and when applied to an unknown response vector in identification mode.

IV. Identification of the Unknown Analyte

As described above, in systems and methods of this invention, a training mode is conducted to measure the characteristics of a variety of known analytes. This information is stored and used as a guideline for identifying unknown analytes in the "identification mode".

In preferred embodiments, the training mode is performed on the same device that is later used to identify the unknown analyte. Such a device can be a handheld device. In other embodiments, the training mode is performed on a separate device. The analyte characteristics are stored on a server and and then downloaded to another device, such as a handheld device, which identifies the unknown analyte by comparing its characteristics to the characteristics generated during the training mode. In yet another embodiment, the collection of characteristics in both the training and identification mode is conducted on a single device, but analysis of the parameters is conducted on a separate computer system. See, U.S. patent application Ser. No. 09/518,179 filed May 26, 2000, which is herein incorporated by reference.

In certain embodiments, the identification comprises exposing an unknown analyte to each sensor, measuring the response of each sensor to the unknown analyte, assembling the response vector for the unknown analyte, applying an importance index vector to the response vector for the unknown analyte, and comparing the weighted response vector for the unknown analyte to the weighted response vectors for the analytes examined in the training mode.

By determining the closest match between the weighted response vector for the unknown analyte and the weighted response vectors for the known analytes or analytes representing a class of analyte, the unknown analyte can be identified as one of the known analytes or as a member of a class of analyte or determined to not be any of the analytes examined in the training mode.

A. Pattern Analysis Techniques/Algorithms

In preferred embodiments, the weighted response vectors for both the unknown and known analytes are analyzed using multivariate pattern recognition algorithms. In one embodiment, measurements using electronic noses of the present invention provide two-dimensional data sets. In this aspect, the rows represent samples and the columns represent responses to a particular sensor. For example, if the number of sensors is 32, there are 32 readings generated for each exposure. The two-dimensional data set is usually called the "X-matrix". The individual variables are called the x or independent variables.

In order to reduce redundancy and noise, it is desirable to generate a smaller data set with fewer variables that contains all the useful information from the 32 variable data set (i.e., the X-matrix). Multivariate pattern recognition algorithms are useful for such data compression and to build models which allow comparison of the response vectors for the unknown and known analytes. Those of skill in the art will appreciate that the use of 32 sensors is merely exemplary, and the present invention is useful for all sensor arrays having at least two sensors.

Numerous pattern recognition algorithms are well known in the art and include, but are not limited to, Principal Component Analysis, K-Nearest Neighbor (KNN), Soft Independent Modeling of Class Analogy (SIMCA), Fisher Linear Discrimination (FLD), kernel-based nonlinear classifiers such as Support Vector Machines (SVM) and Kernel Fisher Discriminants (KFD), Canonical Discriminant Analysis (CDA), Partial Least Squares Discriminant Analysis, genetic algorithms, fuzzy logic and combinations thereof. Such methods can be used in combination or sequentially to compare the response vectors.

In preferred embodiments of these systems and methods, Principal Component Analysis (PCA) is used for outlier diagnosis and KNN and CDA are used for building a model and predicting the identity of the unknown analyte.

For a detailed description of the use of the Fisher Linear Discriminant Analysis method for resolution of odors, see U.S. patent application Ser. No. 09/318,900, which is herein incorporated by reference. For a more detailed description of the use of Principal Component Analysis for resolution of odors, see U.S. Pat. No. 5,571,401, which is herein incorporated by reference.

B. Initial Signal Processing

In preferred embodiments of the present systems and methods, the raw response data for both the known analytes and the unknown analyte is subject to one or more of the following processes, i.e., digital filtering, reduction, normalization, or scaling prior to weighting with an importance index.

In especially preferred embodiments, the data is processed all four ways, i.e., filtered, reduced, normalized, and scaled. Typically the data is sequentially captured, filtered, reduced, normalized, and scaled prior to importance index weighting.

In certain embodiments, these preprocessing steps and application of the importance index to training set data are followed by cross-validation/prediction, a method for ensuring the quality of training set data.

Noise Filtering

Response measurements from sensor arrays are sometimes accompanied by high frequency noise. Since a high signal to noise ratio (SNR) is preferable for pattern recognition, especially when the concentration of sample is low, it is thus desirable to boost the signal relative to the noise using digital filtering techniques. These techniques can improve the reproducibility between exposures. Data can be filtered using any of numerous methods known to those of skill in the art, such as least squares polynomial and Kalman filtering. Preferably, the collected raw data is filtered using a Savitsky-Golay method in order to smooth the response curve using a polynomial fit. In certain embodiments, the filter window is set to give good smoothing without significant distortion.

Reduction

The filtered data can be reduced to a relative change of the response caused by exposure to the analyte using a baseline correction method. An average of base response ($R_o$) can be calculated by taking several data points before the sample exposure and several data points after the sample has been purged from the device. The average maximum response ($R_{max}$) during the sample exposure can be calculated using the absolute maximum response and more data points (e.g., 4) afterwards during the sample exposure. The response of a sensor is defined as:

$$R/R_o = (R_{max} - R_o)/R_o \qquad \text{IIa}$$

Normalization

The sensor arrays used in systems and methods of this invention are often exposed to analytes at high concentration in the training mode, but exposed to unknown analytes at a much lower concentration. To remove the effect of different analyte concentrations, the responses of the sensors can be normalized using any method known to those of skill in the art. In certain embodiments, normalization is conducted using a simple weighting method:

$$\text{normalized}(R/R_o)_i = (R/R_o)_i / \sum_i (R/R_o)_i . \qquad \text{II}$$

where i specifies sensor number from 1 to the number of sensors.

Scaling

To remove any inadvertent weighting that arises due to arbitrary units or variations in the average magnitude of sensor responses, the normalized data can scaled using any method known to those of skill in the art. Common scaling methods include mean centering, variance scaling, or autoscaling (mean centering followed by variance scaling), which is preferred for this method.

Raw data processed via any one or more (e.g., two, three, or four) of the above methods can be used to generate a response vector for a particular exposure to an analyte prior to application of an importance index vector.

V. Sensors & Devices for Detection of Analytes

A. Sensors Used in Systems and Methods of this Invention

The devices, methods, and systems of the present invention include an array of sensors and, in certain instances, the sensors as described in U.S. Pat. No. 5,571,401 are used. Sensors suitable for use in systems and methods of the present invention include, but are not limited to, surface acoustic wave (SAW) sensors; quartz microbalance sensors; Taguchi gas sensors; conductive composite resistors; metal oxide gas sensors, such as tin oxide gas sensors; organic gas sensors; metal oxide field effect transistor (MOSFET); piezoelectric devices; infrared sensors; sintered metal oxide sensors; metal gate MOSFET, such as Pd-gate MOSFET; phthalocyanine sensors; electrochemical cells; conducting polymer sensors; catalytic gas sensors; organic semiconducting gas sensors; solid electrolyte gas sensors; temperature sensors, humidity sensors, piezoelectric quartz crystal sensors; Langmuir-Blodgett film sensors, dye-impregnated polymer films on fiber optic detectors, and combinations thereof.

In a preferred embodiment, the sensors of the present invention are disclosed in U.S. Pat. No. 5,571,401, which is herein incorporated by reference. Briefly, the sensors described therein are conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors and in certain instances 1000 or more sensors. The array of sensors can be formed on an integrated circuit using semiconductor technology methods, an example of which is disclosed in PCT Patent Application Serial No. WO 99/08105, entitled "Techniques and Systems for Analyte Detection," published Feb. 19, 1999, and incorporated herein by reference. Another preferred sensor is disclosed in WO 99/27357 entitled "Materials, Method and Apparatus for Detection and Monitoring Chemical Species," published Jun. 3, 1999.

B. General Operation of Sensor Device

In certain embodiments, the temporal response of each sensor (response as a function of time) is recorded and can be displayed. Various responses include, but are not limited to, frequency, temperature, potential, current, resistance, impedance, capacitance, inductance, magnetic, optical, and the like. The temporal response of each sensor can be normalized to a maximum percent increase and percent decrease that produces a response pattern associated with the exposure of the analyte. By iterative profiling of known analytes, a structure-function database correlating analytes and response profiles is generated. Unknown analytes can then be characterized or identified using response pattern comparison and recognition algorithms. Accordingly, analyte detection systems comprising sensor arrays, a measuring device for detecting responses across each sensor, a computer, a display, a data structure of sensor array response profiles, and a pattern recognition algorithm(s) or comparison tables are provided. In another embodiment, the electrical measuring device or detector is an integrated circuit comprising neural network-based hardware and a digital-analog converter (DAC) multiplexed to each sensor, or a plurality of DACs, each connected to different sensor(s).

In certain instances, the array of sensors is in a handheld device. A suitable handheld device is described in U.S. Pat. No. 6,085,676, issued to Sunshine et al., on Jul. 11, 2000, and incorporated herein by reference in its entirety for all purposes.

EXAMPLES

The following examples are offered to illustrate, but not to limit the claimed invention.

Example 1

This example illustrates the effects of importance index weighting on discrimination and prediction capabilities of an "electronic nose".

In particular, the experiment was conducted on the Cyra-Nose 320, a portable, hand-held electronic nose developed by Cyrano Sciences, Inc., Pasadena, Calif.

The Canonical Discriminant Algorithm was selected as the pattern recognition algorithm with normalization set to NORM1 and preprocessing set to autoscaling. The unit was trained with 10 exposures each for the following six analytes:

TABLE 1

List of Analytes Used in Importance Index Weighting Test

| Class Number | Analyte |
|---|---|
| 1 | Ethylene Glycol |
| 2 | Acetic Acid |
| 3 | Water |
| 4 | Isopropyl Alcohol |
| 5 | Acetone |
| 6 | Ethanol |

Two separate methods were created (a method being defined in this example as a configuration on the device and a corresponding training set)—one called WEIGHTED in which importance index weighting was enabled with weighting power set to 1.0, and the other method called UNWEIGHTED in which importance index weighting was disabled. Both methods had identical training sets and option settings except for the importance index weighting option.

Cross Validation results and interclass distances for both methods are shown in the following table.

TABLE 2

Cross Validation Results for Method WEIGHTED (in which Importance Index Weighting was Enabled)

| | | Identified As | | | | | |
|---|---|---|---|---|---|---|---|
| | | Ethylene | Acetic Acid | Water | IPA | Acetone | Ethanol |
| Trained As | Ethylene | 10 | 0 | 0 | 0 | 0 | 0 |
| | Acetic Acid | 0 | 10 | 0 | 0 | 0 | 0 |
| | Water | 0 | 0 | 10 | 0 | 0 | 0 |
| | IPA | 0 | 0 | 0 | 10 | 0 | 0 |
| | Acetone | 0 | 0 | 0 | 0 | 10 | 0 |
| | Ethanol | 0 | 0 | 0 | 0 | 0 | 10 |

TABLE 2-continued

Cross Validation Results for Method WEIGHTED (in which Importance Index Weighting was Enabled)

| | | |
|---|---|---|
| Correct: | | 100.000% |
| Incorrect: | | 0.000% |

Interclass M-Distances

| | Ethylene | Acetic Acid | Water | IPA | Acetone | Ethanol |
|---|---|---|---|---|---|---|
| Ethylene | | 34.118 | 34.514 | 35.938 | 51.735 | 33.795 |
| Acetic Acid | | | 25.355 | 14.410 | 29.649 | 11.474 |
| Water | | | | 36.410 | 36.237 | 31.444 |
| IPA | | | | | 27.275 | 5.209 |
| Acetone | | | | | | 24.574 |
| Ethanol | | | | | | |

TABLE 3

Cross Validation Results for Method UNWEIGHTED (in which Importance Index Weighting was Disabled)

Identified As

| | | Ethylene | Acetic Acid | Water | IPA | Acetone | Ethanol |
|---|---|---|---|---|---|---|---|
| Trained As | Ethylene | 10 | 0 | 0 | 0 | 0 | 0 |
| | Acetic Acid | 0 | 10 | 0 | 0 | 0 | 0 |
| | Water | 2 | 0 | 8 | 0 | 0 | 0 |
| | IPA | 0 | 0 | 0 | 10 | 0 | 0 |
| | Acetone | 0 | 0 | 0 | 0 | 10 | 0 |
| | Ethanol | 0 | 0 | 0 | 0 | 0 | 10 |

| | | |
|---|---|---|
| Correct: | | 96.667% |
| Incorrect: | | 0.000% |

Interclass M-Distances

| | Ethylene | Acetic Acid | Water | IPA | Acetone | Ethanol |
|---|---|---|---|---|---|---|
| Ethylene | | 17.175 | 8.495 | 27.669 | 18.152 | 22.295 |
| Acetic Acid | | | 18.995 | 15.505 | 19.889 | 10.999 |
| Water | | | | 32.391 | 24.793 | 27.176 |
| IPA | | | | | 23.765 | 5.635 |
| Acetone | | | | | | 9.066 |
| Ethanol | | | | | | |

Average Interclass M-distance is as follows for each method:
WEIGHTED 28.8
UNWEIGHTED 19.5

Note that average interclass distance increased from 19.5 to 28.8 when importance index weighting was enabled, an improvement of 47.7 percent. That fact implies that for this particular training set, importance index weighting resulted (on average) in smaller clusters in canonical space for the exposures to each analyte in the training set, a desirable effect that is usually associated with better prediction results for unknown samples.

Over the next 14 days, 112 exposures were taken in identify mode. Each exposure was identified twice—once using the method WEIGHTED (in which importance index weighting is applied with a power of 1.0), and once using the method UNWEIGHTED (in which importance index weighting is disabled). Of these 112 exposures, 96 were to analytes in the training set and 16 were to analytes not in the training set.

Table 4 shown below contains the results of all exposures in identify mode to analytes in the training set.

TABLE 4

Results Of 96 Identify Exposures to Analytes In the Training Set

| Result | Importance Index Weighting Applied (Method WEIGHTED) | Importance Index Weighting Not Applied (Method UNWEIGHTED) |
|---|---|---|
| predicted correctly | 88 (91.7%) | 80 (83.3%) |
| predicted incorrectly | 3 (3.1%) | 10 (10.4%) |
| predicted as "unknown" | 5 (5.2%) | 6 (6.3%) |

Note that when importance index weighting was applied, the percentage of correct identifications from exposures to analytes in the training increased from 83.3 percent to 91.7 percent. Also, incorrect predictions (identifications resulting in a prediction of the wrong analyte) fell from 10.4 percent to 3.1 percent. Exposures predicted as unknown were similar for both methods.

Table 5 below shows the results of exposures in identify mode to analytes not in the training set. In most cases, these exposures were to perfumes.

TABLE 5

Results Of 16 Identify Exposures to Analytes Not In the Training Set

| Result | Importance Index Weighting Applied (Method WEIGHTED) | Importance Index Weighting Not Applied (Method UNWEIGHTED) |
|---|---|---|
| correctly predicted as unknown | 16 (100%) | 15 (93.8%) |
| misidentified as an analyte in the training set | 0 (0%) | 1 (6.43%) |

Both WEIGHTED and UNWEIGHTED methods were able to effectively reject analytes not in the training set by classifying them as unknown, although for the method where importance index weighting was employed, the results were better (all 16 correct, versus 15 out of 16 correct).

Example 2

This example further illustrates the effect of importance index weighting on the performance of "electronic noses". In particular, it focuses on the effect of raising the importance index to different powers on the discrimination and prediction power of electronic noses.

This study surveyed 17 CyraNose 320 applications, each of which included a training set and a prediction set (defined as a series of exposures to known analytes that were presented to the device in identification mode to test the device). The results for two key parameters described below were among those evaluated during the study, and illustrated in the figures and graphs following in this document.

Discrimination power is a measure of the separation of analytes in a training set when analyzed with a particular configuration on the C320. Discrimination power is measured by mean interclass distance of the exposures in the training set, in canonical space. A larger mean interclass distance implies a training set in which analytes are more clearly separated and distinguishable, and so the training set is more likely to be capable of successfully predicting unknown exposures.

Prediction power is measured by the percentage of exposures in the prediction set which are identified correctly against the corresponding training set.

In the tables and figures immediately following, the Canonical Discriminant Algorithm was used with normalization set to NORM1 and scaling set to "autoscale".

Table 6 below summarizes the results with respect to discrimination and prediction for all 17 applications studied. Columns represent results obtained using a value for iip equal to the value shown in the first row (the column heading). The parameter iip, as defined in this document, is the power to which all importance indices are raised before being multiplied by responses in training and prediction sets. The first column shows the results when iip is zero, the value for which importance index weighting is effectively disabled. The third row shows average interclass distance (discrimination power), and the fourth row shows the percent of exposures in the corresponding prediction set predicted correctly (prediction power). Exposures in the prediction set are sometimes referred to as "unknowns".

TABLE 6

Mean Discrimination and Prediction Power For 17 Datasets

| iip | 0.0 | 0.2 | 0.5 | 1.0 | 1.5 | 2.0 | 3.0 | 4.0 | 5.0 |
|---|---|---|---|---|---|---|---|---|---|
| Minimum Interclass Dist. After Cross Validation | 12.52 | 14.87 | 17.15 | 15.44 | 14.63 | 14.83 | 13.54 | 13.06 | 12.72 |
| Maximum Interclass Dist. After Cross Validation | 30.17 | 34.05 | 39.43 | 38.68 | 35.58 | 35.23 | 32.27 | 31.69 | 31.03 |
| Average Interclass Dist. After Cross Validation | 20.65 | 23.80 | 27.83 | 26.63 | 24.50 | 24.50 | 22.53 | 21.96 | 21.59 |
| % Unknowns Identified Correctly | 68.73 | 72.13 | 74.99 | 79.22 | 76.00 | 74.84 | 72.85 | 71.18 | 66.72 |

Note that prediction power (the value in the last row of the above table) peaked at a value of iip of 1.0, and discrimination power (in the third row of the table) peaked at a value of iip equal to 0.5 (with the value at iip of 1.0 only slightly below the peak value at iip of 0.5).

Figure 1:
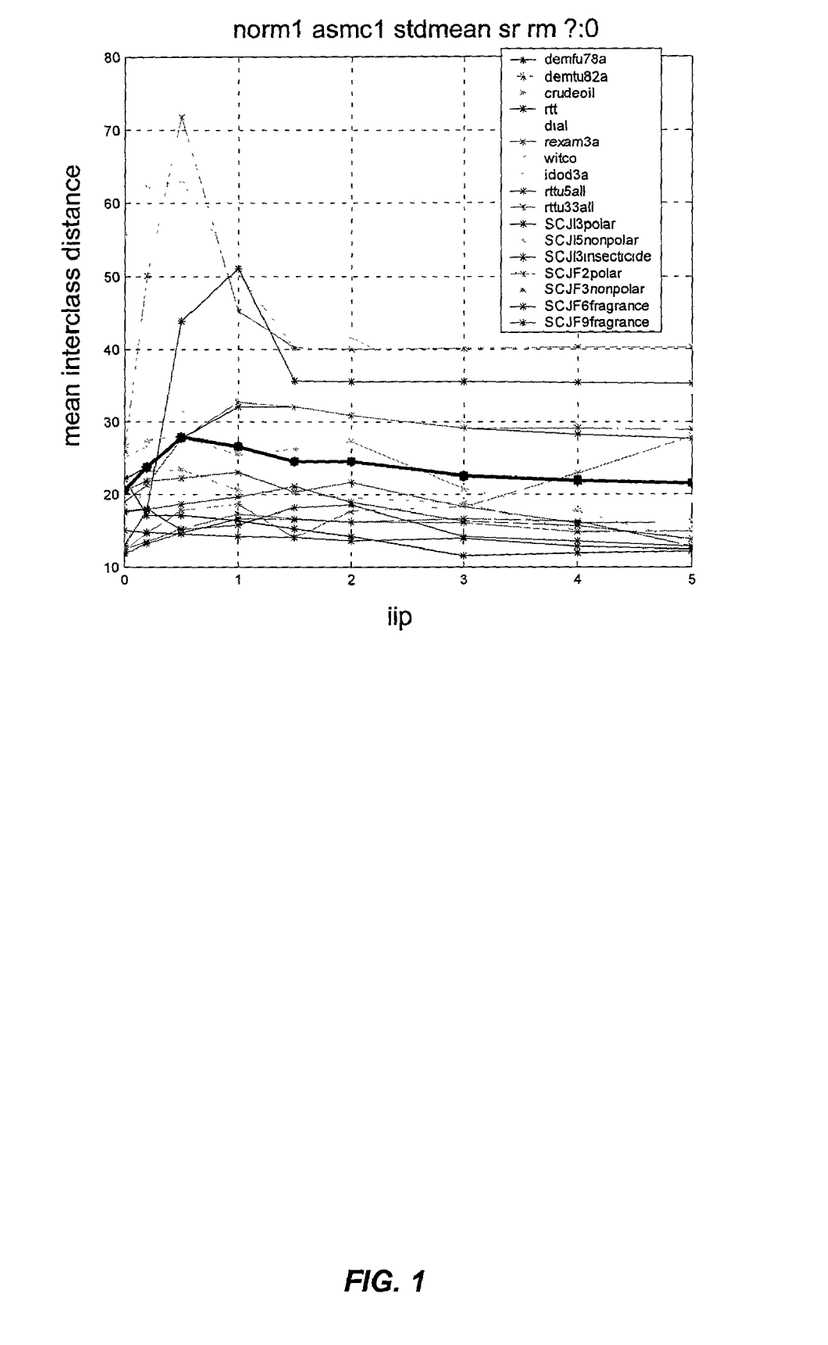
FIG. 1 illustrates the discrimination power (mean interclass distance) for 17 datasets vs. iip.
Figure 2:
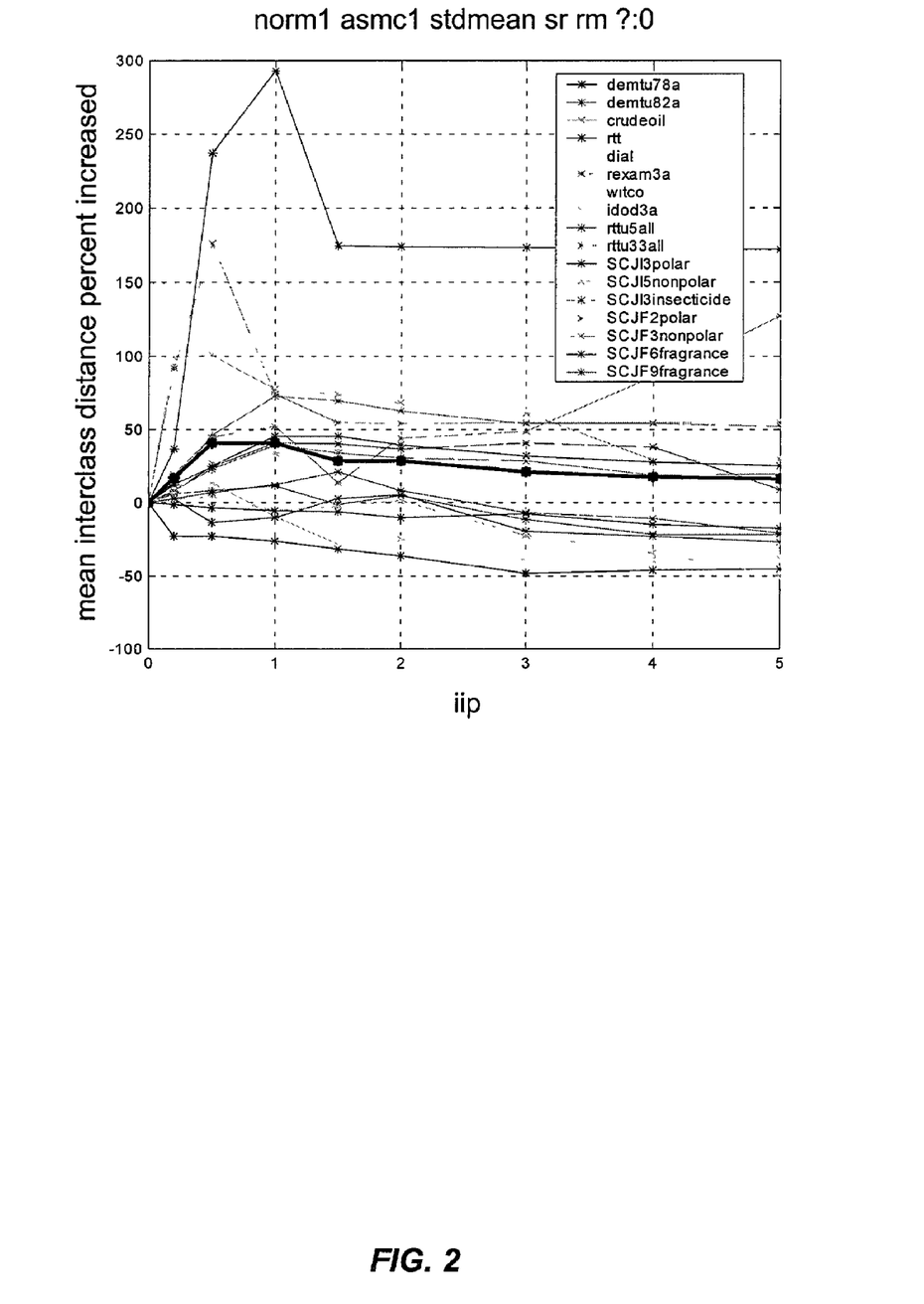
FIG. 2 illustrates the mean interclass distance percentage change relative to unweighted results for 17 datasets vs. iip.
Figure 3:
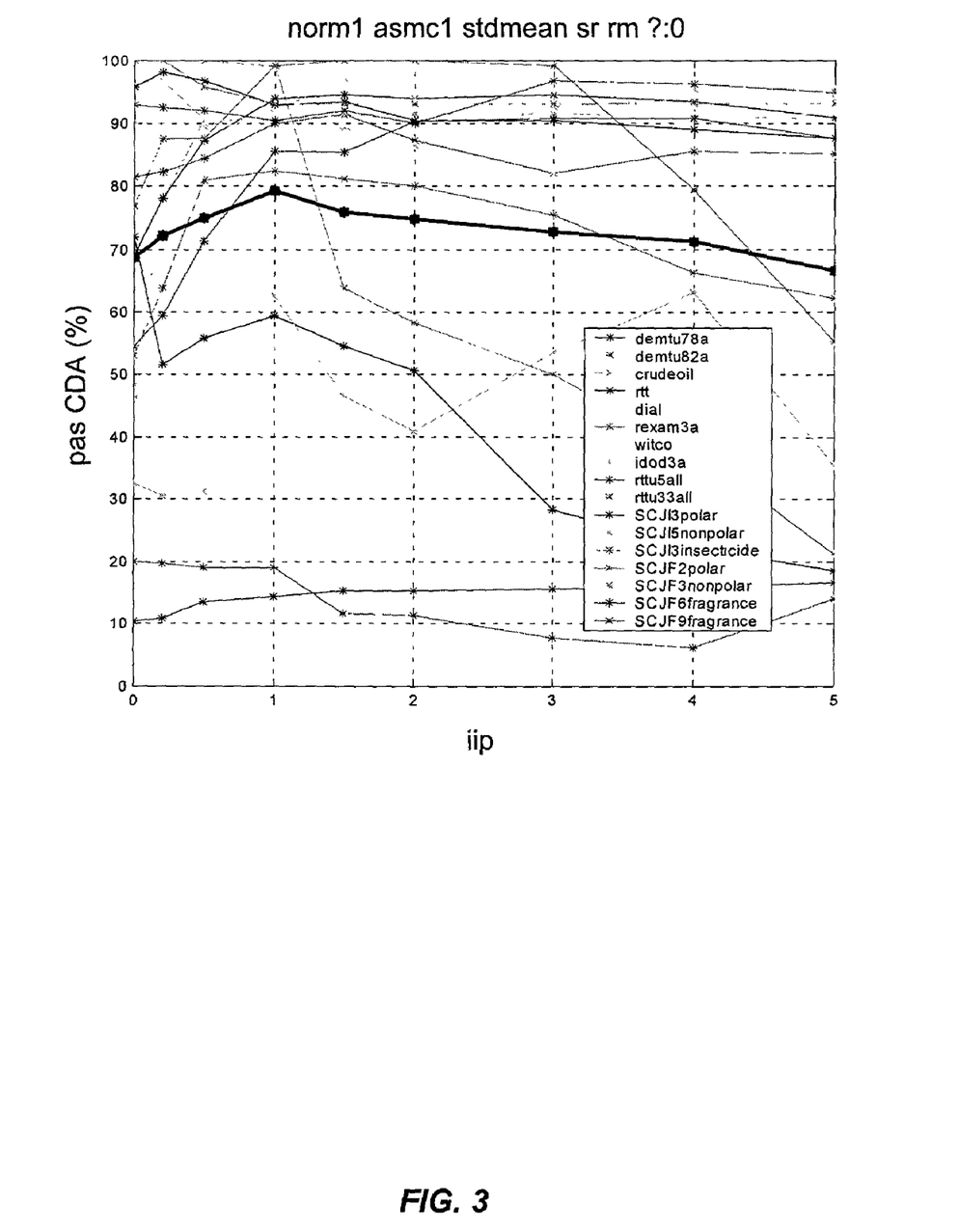
FIG. 3 illustrates the percentage of prediction samples identified correctly for 17 datasets vs. iip.
Figure 4:
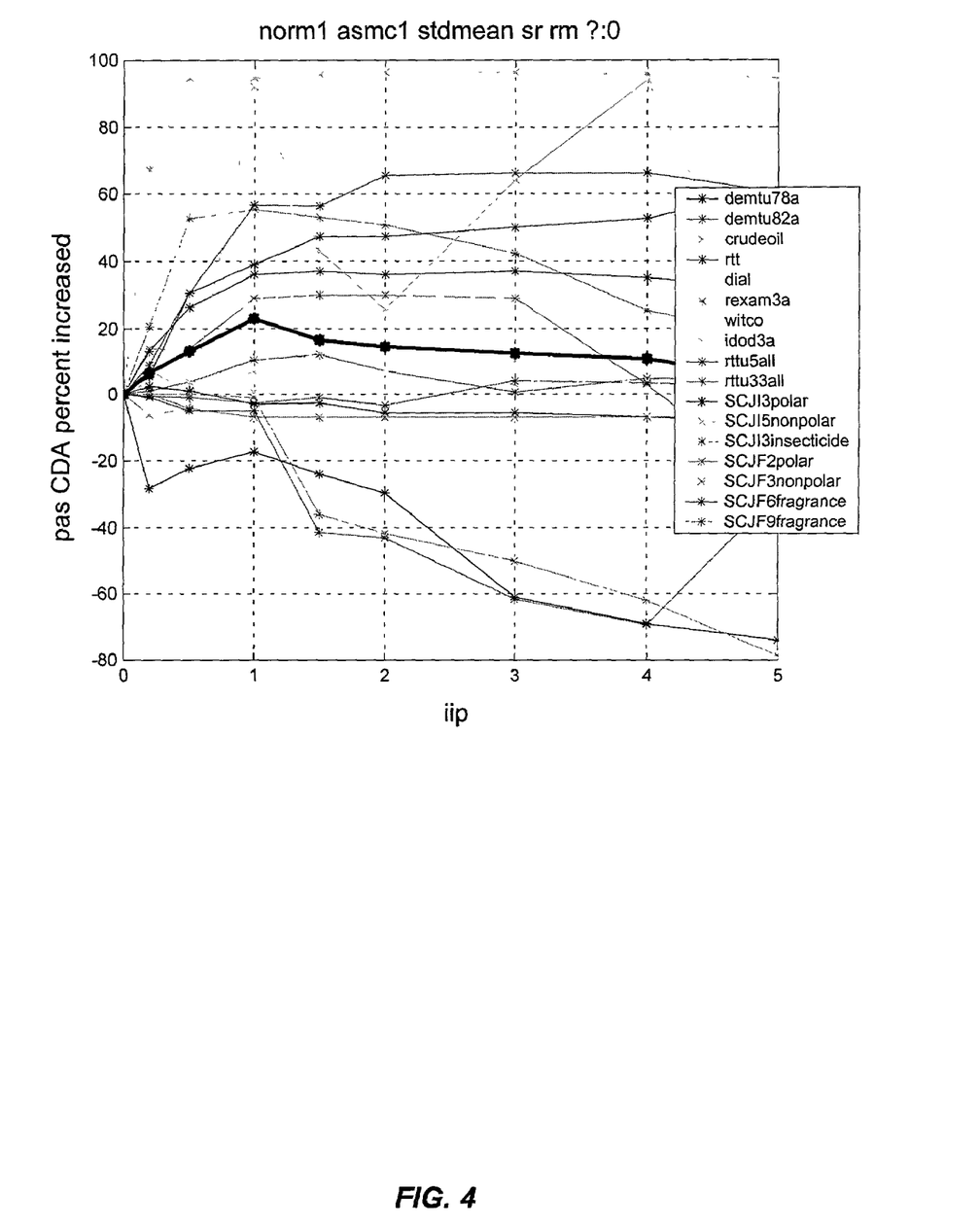
FIG. 4 illustrates the percentage change (relative to unweighted results) of the percentage of prediction samples identified successfully for 17 datasets vs. iip.
Figure 5:
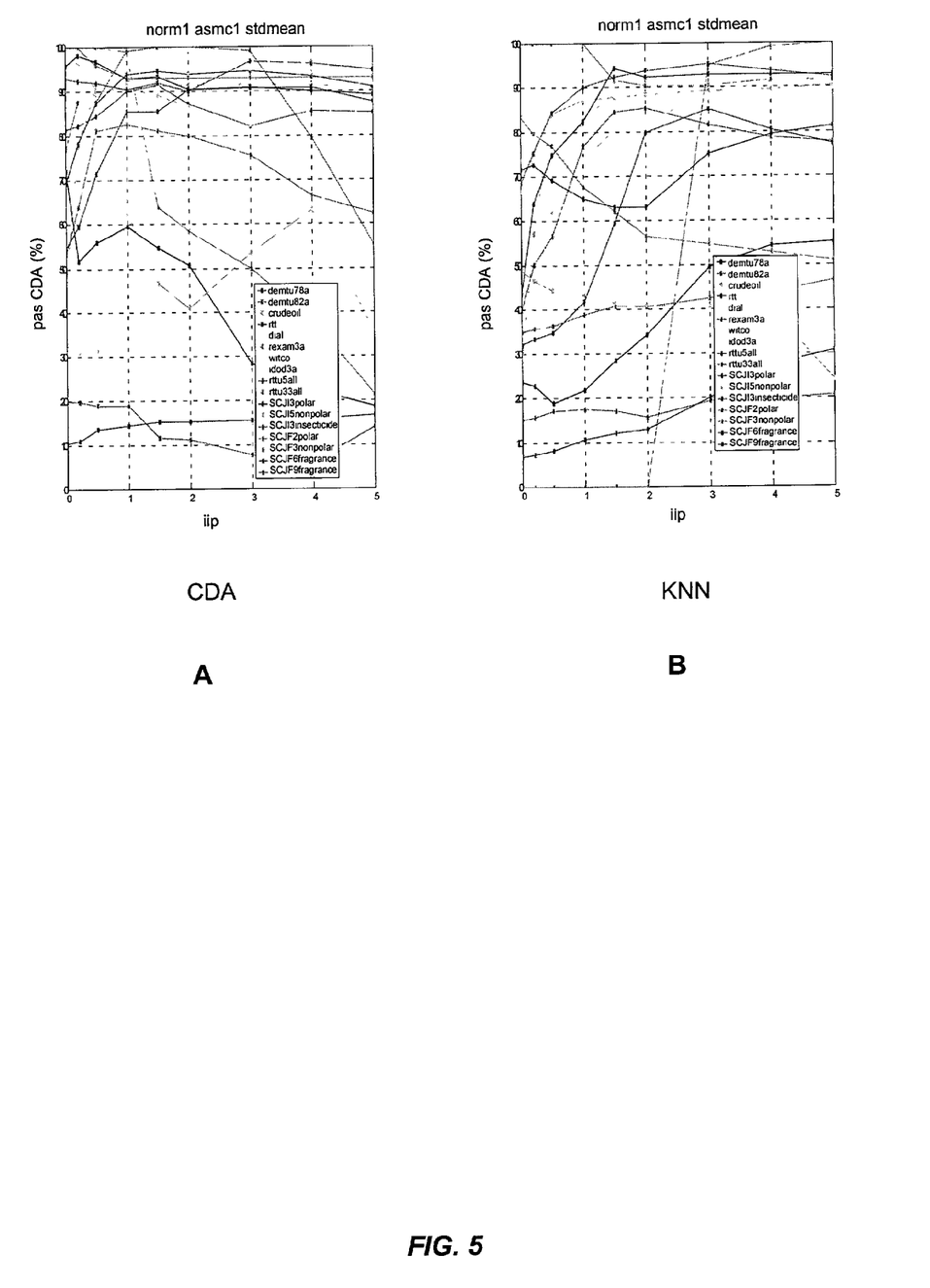
FIGS. 5A–B illustrate the effect of importance index weighting on prediction power when using two different pattern recognition algorithms.
Figure 6:
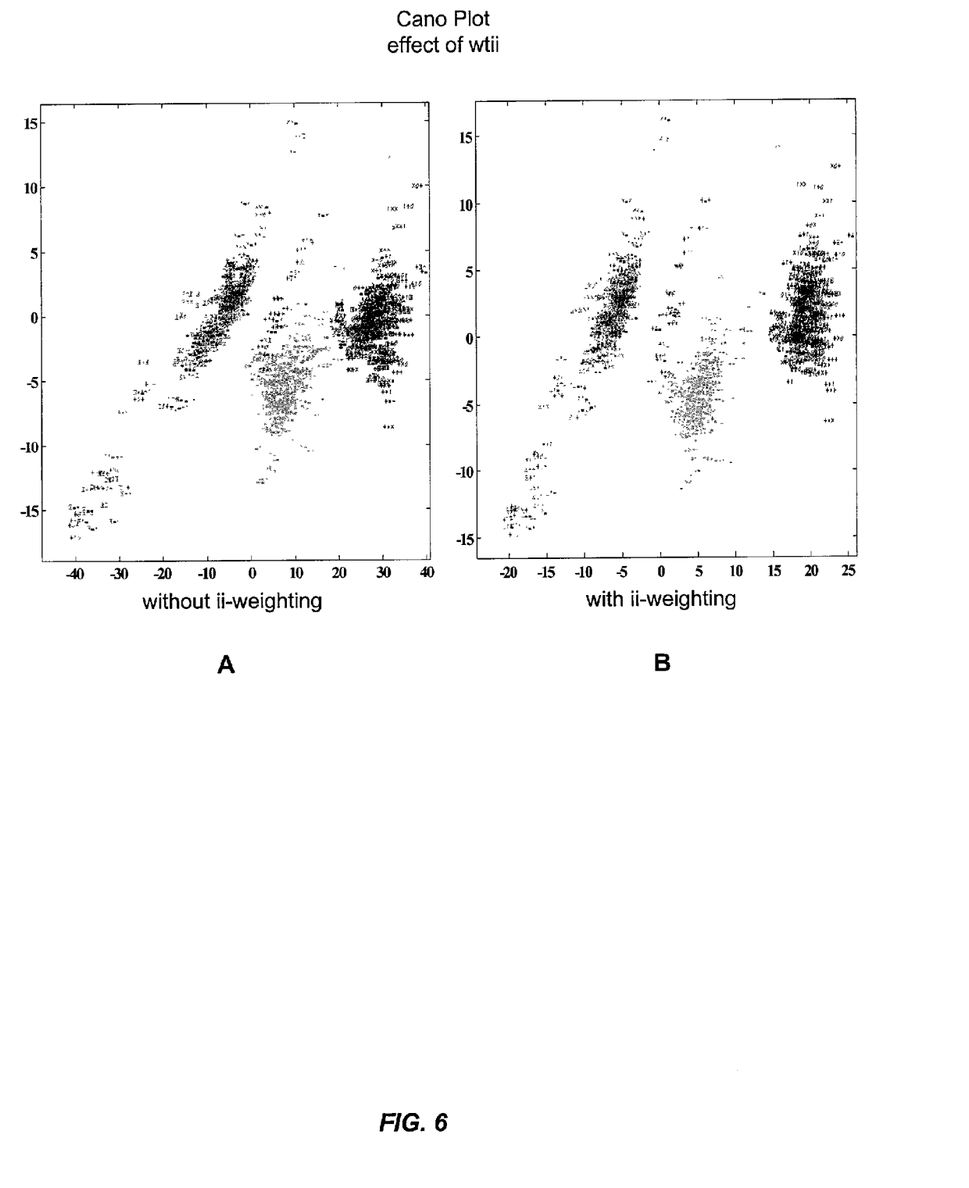
FIGS. 6A–B illustrate the effect of importance index weighting on the separation of the clusters generated by Canonical Discriminant Analysis.

The attached graphs illustrate the effect of importance index weighting on discrimination (as measured by mean interclass distance) for each of the 17 datasets used in the study. The heavy black line is the global mean, or average of the means for each of the 17 datasets. FIG. 1 illustrates the discrimination power (mean interclass distance) for 17 datasets vs. iip. FIG. 2 illustrates the mean interclass distance percentage change relative to unweighted results for 17 datasets vs. iip. FIG. 3 illustrates the percentage of prediction samples identified correctly for 17 datasets vs. iip. FIG. 4 illustrates the percentage change (relative to unweighted results) of the percentage of prediction samples identified successfully for 17 datasets vs. iip. FIG. 5 contrasts the effect of importance index weighting on prediction power when using two different pattern recognition algorithms. The graph on the left shows results using Canonical Discriminant Analysis as the pattern recognition algorithm; the graph on the right shows results using the KNN algorithm. The X-axis shows the value of iip.

The following two tables summarize the effect of importance index weighting on the 17 applications in a slightly different way. Table 7 relates to discrimination power as measured by mean interclass distance, and Table 8 relates to prediction power as measured by the percentage of exposures in the prediction set identified correctly. Columns show the number of applications satisfying the listed criterion for different values of iip.

Each of these tables has three rows, which divide the 17 applications into three categories (one category per row):
1) The first row shows the number of applications (out of 17) in which importance index weighting improved the parameter being studied by 5 percent or more.
2) The second row shows the number of applications where importance index weighting had minimal effect (parameter changed by less than 5 percent).
3) The third row shows the number of applications where importance index weighting decreased the parameter being studied by 5 percent or more.

TABLE 7

Effect of Importance Index Weighting on Discrimination vs. iip as Measured by Number of Applications Having At Least a 5% Change in Mean Interclass Distance Compared to the Unweighted Result

| iip | 0.2 | 0.5 | 1.0 | 1.5 | 2.0 | 3.0 | 4.0 | 5.0 |
|---|---|---|---|---|---|---|---|---|
| # Applications Where IIW Improved Discrimination by at least 5% | 11 | 12 | 11 | 10 | 11 | 9 | 9 | 9 |
| # Applications Where IIW Had Minimal Effect | 4 | 2 | 0 | 3 | 2 | 0 | 0 | 0 |
| # Applications Where IIW Reduced Discrimination by at least 5% | 2 | 3 | 6 | 4 | 4 | 8 | 8 | 8 |

TABLE 8

Effect of Importance Index Weighting on Prediction vs. up as Measured by Number of Applications Having At Least a 5% Change in Percent of Prediction Set Identified Correctly Compared to the Unweighted Result (Nom1, Autoscaled)

| iip | 0.2 | 0.5 | 1.0 | 1.5 | 2.0 | 3.0 | 4.0 | 5.0 |
|---|---|---|---|---|---|---|---|---|
| # Applications Where IIW Improved % ID'd correctly by at least 5% | 7 | 6 | 9 | 9 | 10 | 8 | 7 | 7 |
| # Applications Where IIW Had Minimal Effect on % ID'd correctly | 8 | 10 | 6 | 4 | 2 | 3 | 5 | 4 |
| # Applications Where IIW Reduced % ID'd correctly by at least 5% | 2 | 1 | 2 | 4 | 5 | 6 | 5 | 6 |

Based on Tables 7 and 8 shown above, the majority of applications showed improvement in both discrimination and prediction with importance index weighting applied, especially when iip was set to a value of 1.0.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for analyzing an analyte, said method comprising:
   a) disposing a plurality of d sensors in an array, each sensor having a different response to said analyte:
   b) exposing said d sensors to said analyte to generate a response vector for said analyte;
   c) applying an importance index vector to said response vector to generate a weighted response vector; and
   d) comparing said weighted response vector to a weighted training set and thereafter selecting a match to identify said analyte,
   wherein said importance index vector is generated after a training mode conducted on said d sensors and before identification of said analyte,
   wherein said importance index vector is the collection of importance indices for each sensor and the weighted training set is generated by application of the importance index to each said response vector for each exposure to each of said plurality of known analytes in a training set, and
   wherein said importance index for a particular sensor is calculated from all the responses for that sensor in a training set as follows:

$$\sqrt{\frac{S^2_{OverallWithinAnalytes}}{S^2_{OverallWithinAnalytes}}}$$

wherein $S^2_{OverallAmongAnalytes}$ is the overall variance among the analytes and $S^2_{Overall\ WithinAnalytes}$ is the overall variance within the analytes.

2. The method of claim 1, wherein $S^2_{OverallAmongAnalyses}$ equals:

$$\frac{1}{k-1}\sum_{i=1}^{k}\left(\overline{x}_i - \overline{\overline{x}}\right)^2 \qquad \text{Ia}$$

and $S^2_{Overall\ WithinAnalytes}$ equals.

$$\frac{1}{k}\sum_{i=1}^{k}\sum_{j=1}^{m(i)}\frac{(x_{ij}-\overline{x}_i)^2}{m(i)-1} \qquad \text{Ib}$$

and wherein
   k is the number of analytes in the training set;
   i is an index over analytes in the training set and ranges from 1 to k;
   m(i) is the number of exposures in the training set for the i th analyte;
   j represents an exposure number in the training set to the i th analyte, and ranges from 1 to m(i);
   $x_{ij}$ is the response in the j th exposure to the i th analyte in the training set for the sensor whose importance index is being calculated;

$$\overline{x}_i$$

is the mean value of all exposures in the training set to the i th analyte for the sensor whose importance index is being calculated; and $\bar{\bar{x}}$ is the mean value of all responses in the training set for the sensor whose importance index is being calculated.

3. A method for analyzing an analyte, said method comprising:
 a) disposing a plurality of d sensors in an array, each sensor having a different response to said analyte;
 b) exposing said d sensors to said analyte to generate a response vector for said analyte;
 c) applying an importance index vector to said response vector to generate a weighted response vector; and
 d) comparing said weighted response vector to a weighted training set and thereafter selecting a match to identify said analyte,
 wherein said importance index vector is generated after a training mode conducted on said d sensors and before identification of said analyte,
 wherein said importance index vector is the collection of importance indices for each sensor and the weighted training set is generated by application of the importance index to each said response vector for each exposure to each of said plurality of known analytes in a training set, and
 wherein the application of said importance index vector to the response vector to generate a weighted response vector comprises:
 a) raising the importance index for each sensor to a certain power;
 b) multiplying each response in the response vector by the importance index for the corresponding sensor raised to a certain power to yield a weighted response; and
 c) assembling the weighted responses to generate a weighted response vector.

4. A method for analyzing an analyte, said method comprising:
 a) disposing a plurality of d sensors in an array, each sensor having a different response to said analyte;
 b) exposing said d sensors to said analyte to generate a response vector for said analyte;
 c) applying an importance index vector to said response vector to generate a weighted response vector; and
 d) comparing said weighted response vector to a weighted training set and thereafter selecting a match to identify said analyte,
 wherein said importance index vector is generated after a training mode conducted on said d sensors and before identification of said analyte,
 wherein said importance index vector is the collection of importance indices for each sensor and the weighted training set is generated by application of the importance index to each said response vector for each exposure to each of said plurality of known analytes in a training set, and
 wherein the application of said importance index vector to the training set to generate a weighted training set comprises:
 a) raising the importance index for each sensor to a certain power;
 b) multiplying each response in the response vector for the training set by said importance index for the corresponding sensor raised to a certain power to yield a weighted response; and
 c) assembling the weighted responses to generate a weighted response vector.

5. The method of claim 3, wherein said importance index is raised to the first power.

6. A method for identifying an unknown analyte, comprising:
 a) disposing a plurality of d sensors in a array, each having a different response to different analytes;
 b) exposing said d sensors two or more times to a plurality of known analytes and measuring the responses from each sensor to each exposure to create a first training set, wherein said first training set contains a response vector for each exposure to each of said plurality of known analytes;
 c) generating a first importance index for each sensor;
 d) selecting a subset of sensors having first importance indices above a certain threshold;
 e) generating a second training set, wherein said second training set consists of all the response vectors in the first training set but with responses to those sensors not passing the selection criterion removed;
 f) calculating a second importance index based on the second training set and assembling a second importance index vector;
 g) applying the second importance index vector to the second training set to generate a second weighted training set;
 h) exposing said subset of sensors to said unknown analyte to generate a response vector for said unknown analyte;
 i) applying said second importance index vector to said response vector for the unknown analyte to obtain a weighted response vector; and
 j) comparing said weighted response vector to the second weighted training set, and then selecting the best match thereby identifying said analyte.

7. A method for identifying an unknown analyte, said method comprising:
 a) disposing a plurality of d sensors in a array, each having a different response to different analytes;
 b) exposing said d sensors two or more times to a plurality of known analytes and measuring the responses from each sensor to each exposure to create a first training set, wherein said first training set contains a response vector for each exposure to each of said plurality of known analytes;
 c) generating an first importance index for each sensor;
 d) identifying a subset of sensors with importance indices above a certain threshold;
 e) generating a second training set, wherein said second training set consists of all the response vectors in the first training set but with responses to those sensors not passing the selection criterion removed;
 f) exposing said subset of sensors to said unknown analyte to generate a response vector; and
 g) comparing said response vector for the unknown analyte to response vectors in the second training set, and thereafter selecting the best match to identify said unknown analyte.

* * * * *